United States Patent
Bromberg et al.

(10) Patent No.: US 6,327,329 B1
(45) Date of Patent: Dec. 4, 2001

(54) METHODS AND APPARATUS FOR MONITORING DETECTOR IMAGE QUALITY

(75) Inventors: Neil B. Bromberg, Milwaukee; Hui David He, Waukesha; Mary Sue Kulpins, New Berlin, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/140,110

(22) Filed: Aug. 25, 1998

(51) Int. Cl.[7] ............... A61B 6/00; H05B 1/64; G01D 18/00
(52) U.S. Cl. ............... 378/19
(58) Field of Search ............... 378/19, 207, 18, 378/4, 90.1, 98.8

(56) References Cited

U.S. PATENT DOCUMENTS

| | | | |
|---|---|---|---|
| 5,430,785 | * 7/1995 | Pfoh et al. | 378/19 |
| 5,473,663 | * 12/1995 | Hsieh | 378/207 |
| 5,521,482 | * 5/1996 | Lang et al. | 318/800 |
| 5,734,691 | * 3/1998 | Hu et al. | 378/4 |
| 5,845,003 | 12/1998 | Hu et al. | |
| 6,115,448 | 9/2000 | Hoffman | |
| 6,134,292 | 10/2000 | Hsieh | |

\* cited by examiner

Primary Examiner—Robert H. Kim
Assistant Examiner—Armando Rodriguez
(74) Attorney, Agent, or Firm—Armstrong Teasdale, LLP; Christian G. Cabou

(57) ABSTRACT

Methods and apparatus for detecting cell to cell variation to ensure that the maximum allowable channel to channel variation is not exceeded are described. In one embodiment, an algorithm is periodically executed to measure the relative gains in the channels. The gains are measured, for example, by recording the signal from an air scan and normalizing to a common reference. Part of the normalization process includes accounting for the non uniformity of the x-ray beam, for example, the heel effect. It is assumed that the x-ray flux profile in z is slowly changing in the x-direction and is obtained by low pass filtering in x. The normalized values are then compared to a predetermined specification. If any particular cell is not within the specification parameters, then the module in which such cell resides may be replaced. In addition to measuring gain variation and comparing it to a specification, a trending analysis also may be performed. The trending algorithm predicts the time at which the detector will fail the specification so that replacement of the detector may take place before failure occurs.

27 Claims, 3 Drawing Sheets

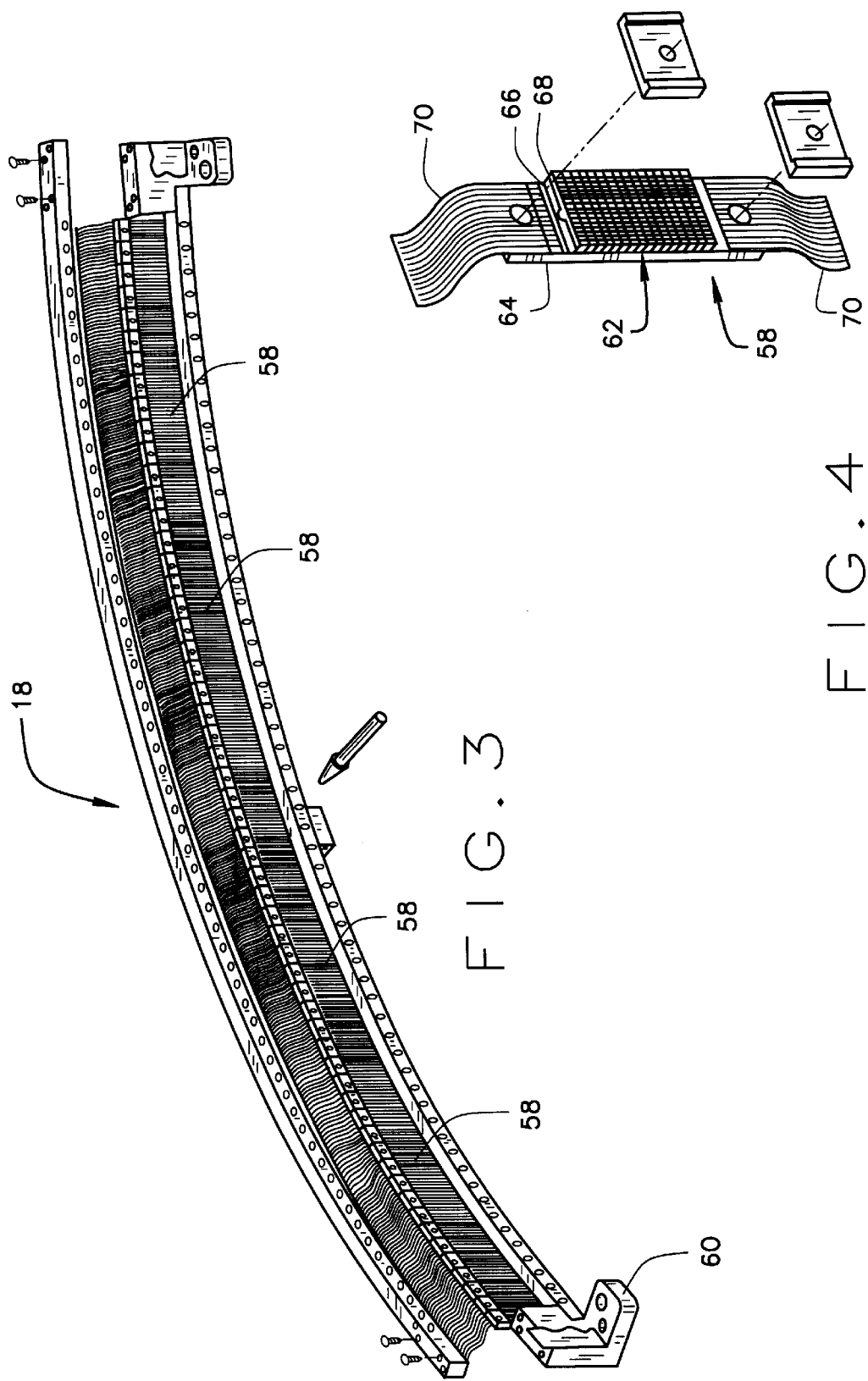

METHODS AND APPARATUS FOR MONITORING DETECTOR IMAGE QUALITY

BACKGROUND OF THE INVENTION

This invention relates generally to imaging and, more particularly, to monitoring performance of a detector in an imaging system.

In at least some known medical imaging systems, such as a computed tomograph (CT) imaging system, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a post patient collimator for collimating scattered x-ray beams received at the detector. A scintillator is located adjacent the post patient collimator, and photodiodes are positioned adjacent the scintillator.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

The channels of the detector typically are ganged together to form the rows. Channel to channel variation in the z-direction can result in generation of image artifacts. As the detector ages the gain variation changes due to radiation damage. Corrections for such channel to channel variability are know, but the effectiveness of such corrections depend on the magnitude of the variability.

BRIEF SUMMARY OF THE INVENTION

These and other objects may be attained by an algorithm, which may be executed periodically by the imaging system, for detecting cell to cell variation to ensure that the maximum allowable channel to channel variation is not exceeded. More specifically, and in accordance with one aspect of the present invention, an algorithm is periodically executed to measure the relative gains in the channels. The gains are measured, for example, by recording the signal from an air scan and normalizing to a common reference. Part of the normalization process includes accounting for the non uniformity of the x-ray beam, for example, the heel effect. It is assumed that the x-ray flux profile in z is slowly changing in the x-direction and is obtained by low pass filtering in x. The normalized values are then compared to a predetermined specification. If any particular cell is not within the specification parameters, then the module in which such cell resides may be replaced.

In addition to measuring gain variation and comparing it to a specification, a trending analysis also may be performed. The trending algorithm predicts the time at which the detector will fail the specification so that replacement of the detector may take place before failure occurs.

BRIEF DESCRIPTION OF THE DRAWINGS

FIG. 3 is a perspective view of a CT system detector array.

FIG. 4 is a perspective view of a detector module.

DETAILED DESCRIPTION OF THE INVENTION

Set forth below is a description of an exemplary multislice CT system in accordance with one embodiment of the present invention. Although one embodiment of the system is described in detail below, it should be understood that many alternative embodiments of the inventions are possible. For example, although one particular detector is described, the present invention could be utilized in connection with other detectors, and the present invention is not limited to practice with any one particular type of multislice detector. Specifically, the detector described below includes a plurality of modules and each module includes a plurality of detector cells. Rather than the specific detector described below, a detector which has multiple modules with multiple elements along the x-axis and/or z-axis joined together in either direction to acquire multislice scan data simultaneously, can be utilized. Generally, the system is operable in a multislice mode to collect 1 or more slices of data. Axial and helical scans can be performed with the system, and cross section images of a scanned object can be processed, reconstructed, displayed and/or archived.

Figure 1:
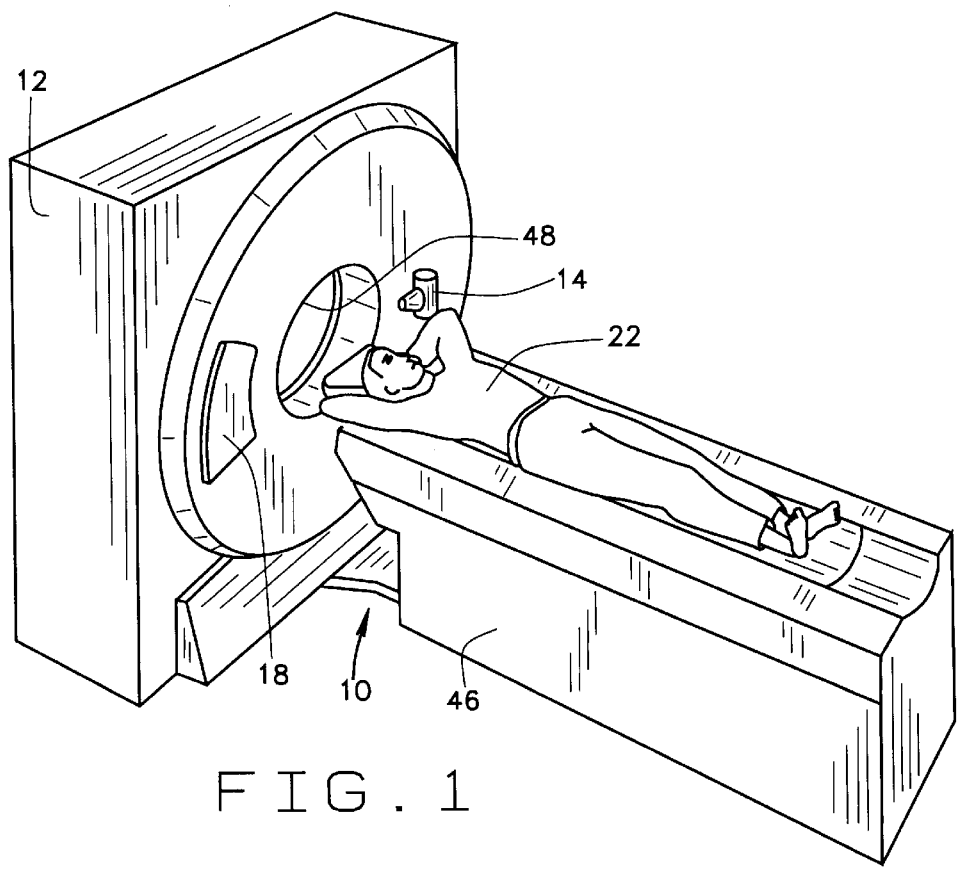
FIG. 1 is a pictorial view of a CT imaging system.
Figure 2:
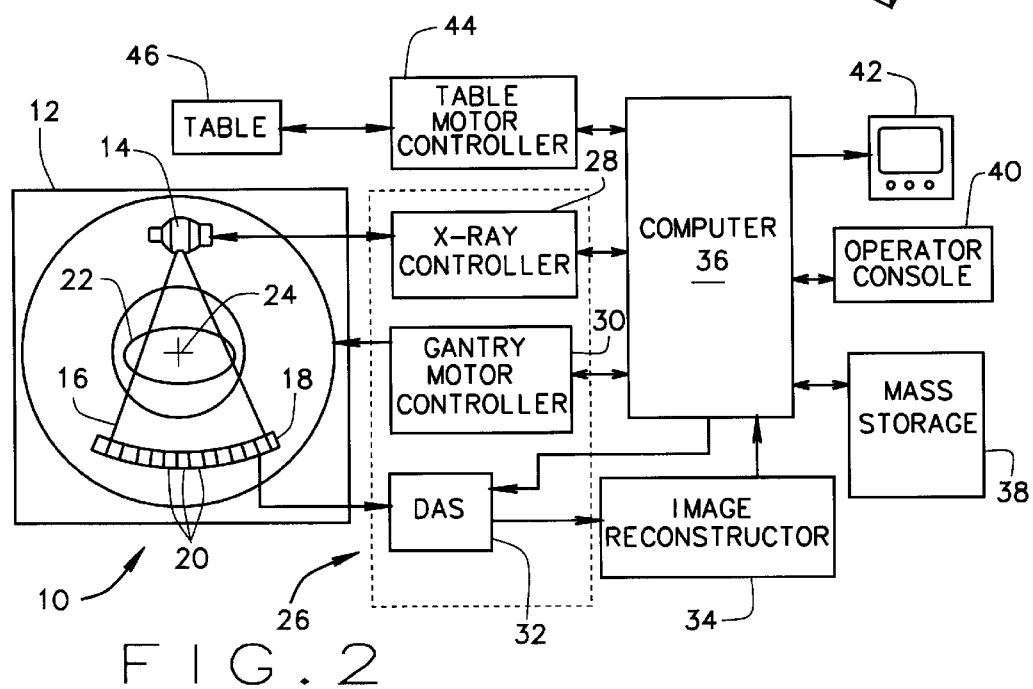
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

As shown in FIGS. 3 and 4, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disabled, or combined so that specific outputs of the photodiode array are electrically connected to CT system DAS 32. In one embodiment defined as a 16 slice mode, decoder 68 enables switch apparatus 66 so that all rows of the photodiode array are electrically connected to DAS 32, resulting in 16 separate, simultaneous slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5:
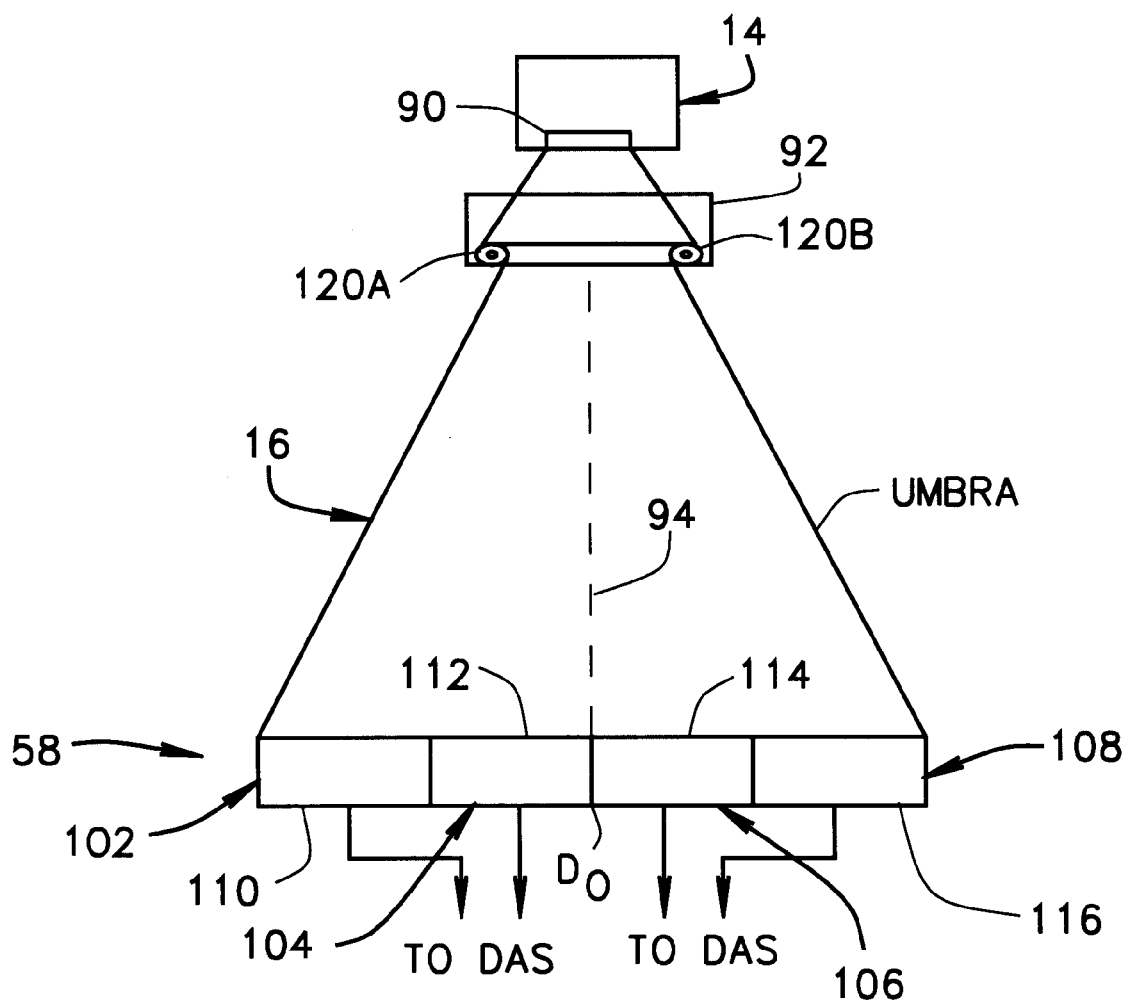
FIG. 5 is a schematic view of the CT imaging system shown in FIG. 1.

FIG. 5 is a simplified schematic view of a "four (or quad) slice" system in that four rows 102, 104, 106 and 108 of detector cells are utilized to obtain projection data. Detector cells 110, 112, 114 and 116 form rows 102, 103, 106 and 108. Each detector cell 110, 112, 114, and 116 illustrated in FIG. 5 may actually be composed of a number of cells (e.g., four) ganged together to produce one output which is supplied to DAS 32.

In one embodiment, collimator 92 includes eccentric cams 120A and 120B. The position of cams 120A and 120B are controlled by x-ray controller 28. Cams 120A and 120B are positioned on opposing sides of fan beam plane 94 and may be independently adjusted with respect to the spacing between cams 120A and 120B and their location relative to fan beam plane 94. Cams 120A and 120B may be positioned with a single cam drive, or alternatively, each cam may be positioned with a separate cam drive, for example a motor. Cams 120A and 120B are fabricated from an x-ray absorbing material, for example, tungsten.

As a result of the eccentric shape, the rotation of respective cams 120A and 120B alters the z-axis profile of x-ray beam 16. More specifically, altering position of cams 120A and 120B alters the position and width of x-ray beam umbra. Particularly, as a result of the jointly stepping eccentric shape of cams 120A and 120B, the total width of x-ray beam umbra is altered. Altering the position, or stepping, cam 120A, alone, alters the umbra width and position relative to one edge of detector array 18. Altering the position of cam 120B, alone, alters the umbra width and position relative to the other, or second edge, of detector array 18 so that the x-ray dosage received by patient 22 is reduced.

In operation, x-ray source 14 is fixed, or placed in a stationary position, and respective cams 120A and 120B are placed in nominal positions so that an x-ray beam 16 is radiated through collimator 92 toward detector array 18. Data is then collected from detector array 18 for a series of steps, or positions of respective cam 120A and 120B. By altering aperture of collimator 92, particularly adjusting cams 120A and 120B, an optimal x-ray beam is radiated onto detector array 18 to produce proper signal intensities from cells 110, 112, 114 and 116.

As explained above, as detector cells 110, 112, 114, and 116 age, the gain variation from channel to channel changes. In order to ensure that the maximum allowable channel to channel variation is not exceeded, and in accordance with one aspect of the present invention, an algorithm is periodically executed to measure the relative gains in the channels. These gains are measured by recording the signal from an air scan and normalizing to a common reference. Part of the normalization process includes accounting for the non uniformity of the x-ray beam, for example, the heel effect. It is assumed that the x-ray flux profile in z is slowly changing in the x-direction and is obtained by low pass filtering in x. The normalized values are then compared to a predetermined specification. If any particular cell is not within the specification parameters, then the module in which such cell resides may be replaced.

In one particular embodiment, a z-slope correction on the collected data is performed. Specifically, and starting from individual cell measurements obtained via air-scan and view averaging, after offset subtraction and reference channel normalization:

$$\{X_{l,i}\}1,\ldots,16; i=1,\ldots,\text{Nchannel}.$$

"x" averages are then defined for the gain: nominal gain profile definition, including normalization to the maximum in the column: where nave is the (odd) number of channels to be used for the nominal gain definition "x" moving $$bp_l(i) = \frac{1}{nave} \sum_{k=i-(nave-1)/2}^{k=i+(nave-1)/2} \left[ \frac{X_{l,k}}{\max_{1 \le l \le 16} X_{l,l}} \right]$$

Normalization to the maximum in z then leads to the following expression:

$$BP_l(i) = \frac{bp_l(i)}{\max_{1 \le l \le 16} bp_l(i)}$$

The nominal gain can then be defined by:

$$G_{i,l} = G_l(i) = \frac{\left(\frac{X_{l,i}}{\max_{1 \le l \le 16} X_{l,i}}\right)}{BP_l(i)}$$

These nominal gain are the inputs for the z-slope correction algorithm.

Nominal gains are required in modeling slow "x" variations that by themselves do not lead to slope related artifacts in the image, but if not accounted for in the correction process, can lead to instabilities. Three examples are (1) twin nominal gain profile, at the scintillator edge, (2) x-ray beam z-profile due to the heel effect, and (3) partial illumination condition, as induced by the use of the beam penumbra for a contemplated low dose mode of operation. The elements of G fall within a range of numbers which are close to 1. The exact boundaries of the range are determined empirically.

In addition to measuring gain variation and comparing it to a specification, a trending analysis also may be performed. The trending algorithm predicts the time at which the detector will fail the specification so that replacement of the detector may take place before failure occurs. The trending algorithm assumes a pattern of usage which is constant in time and for the specific detector in use the aging of the detector elements occur in a linear fashion. A least squares fit to a linear model is made to each element of the gain matrix as a function of time. In general the nature of the trending algorithm depends on the aging characteristics of the detector material.

The data can be remotely retrieved and analyzed from the multislice scanner, e.g., from an automated support center. For example, the data may be retrieved using a PPP modem connection over the phone lines.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for monitoring cell to cell variation in a detector of a computed tomography system, the system including an x-ray source for producing an x-ray beam along an imaging plane, the detector including a plurality of detector cells extending in a z-axis and arranged in a plurality of dectector cell modules, said method comprising:
    performing an air scan;
    obtaining data from the detector cells from the air scan;
    comparing the cell data to a specification to determine cells not within parameters of the specification; and
    replacing a detector cell module in which a detector cell is not within the specification parameters.

2. A method in accordance with claim 1 wherein performing a scan comprises performing an air scan.

3. A method in accordance with claim 1 wherein prior to comparing the cell data to a specification, said method further comprises normalizing the cell data.

4. A method in accordance with claim 3 wherein normalizing the cell data includes compensating for non uniformity of the x-ray beam.

5. A method in accordance with claim 1 wherein the detector is a multislice detector.

6. A method for monitoring cell to cell variation in a detector of a computed tomography system, the system including an x-ray source for producing an x-ray beam along an imaging plane, the detector including a plurality of detector cells extending in a z-axis and arranged in a plurality of detector cell modules, said method comprising:
    performing an air scan;
    obtaining data from the detector cells;
    performing a trending analysis to predict when a detector will fail the specification;
    comparing the cell data to a specification to determine cells not within parameters of the specification; and
    replacing a detector cell module in which a detector cell is not within the specification parameters.

7. An imaging system comprising an x-ray source and at least one multislice detector module, each detector module including a plurality of detector cells extending in a z-axis and arranged in a plurality of detector cell modules, said system configured to:
    perform an air scan;
    obtain data from the detector cells from the air scan; and
    compare the cell data to a specification,
    and further wherein said plurality of detector cell modules are configured to be replaceable when a cell within a module is determined to be outside of parameters of the specification.

8. A system in accordance with claim 7 wherein the scan is an air scan.

9. A system in accordance with claim 7 wherein said system is further configured to normalize the cell data.

10. A system in accordance with claim 9 wherein said system is further configured to compensate for non uniformity of the x-ray beam.

11. A system in accordance with claim 7 wherein said detector is a multislice detector.

12. An imaging system comprising an x-ray source and at least one multislice detector module, each detector module including a plurality of detector cells extending in a z-axis and arranged in a plurality of detector cell modules, said system configured to:

perform a scan;

obtain data from the detector cells;

compare the cell data to a specification; and perform a trending analysis to predict when a detector will fail the specification;

said plurality of detector cell modules configured to be replaceable when a cell within a module is determined to be outside of parameters of the specification.

13. A system in accordance with claim 12 further comprising a remote support center for initiating performance of the air scan.

14. A multislice computed tomography system comprising an x-ray source for producing an x-ray beam along an imaging plane and a detector comprising a plurality of detector cells extending in a z-axis and arranged in a plurality of detector cell modules, said system configured to monitor cell to cell gain variations by:

performing an air scan;

obtaining data from the detector cells for the air scan;

comparing the cell data to a specification, and further wherein said plurality of detector cell modules are configured to be replaceable when a cell within a module is determined to be outside of parameters of the specification.

15. A system in accordance with claim 14 wherein the scan is an air scan.

16. A system in accordance with claim 14 wherein said system is further configured to normalize the cell data.

17. A system in accordance with claim 16 further configured to compensate for non uniformity of the x-ray beam.

18. A multislice computed tomography system comprising an x-ray source for producing an x-ray beam along an imaging plane and a detector comprising a plurality of detector cells extending in a z-axis and arranged in a plurality of detector cell modules, said system configured to monitor cell to cell gain variations by:

performing an air scan;

obtaining data from the detector cells for the air scan;

comparing the cell data to a specification; and performing a trending analysis to predict when a detector will fail the specification;

said plurality of detector cell modules configured to be replaceable when a cell within a module is determined to be outside of parameters of the specification.

19. A system in accordance with claim 18 further comprising a remote support center for initiating performance of the air scan.

20. A method for monitoring cell to cell variation in a detector of a computed tomography system, the system including an x-ray source for producing an x-ray beam along an imaging plane, the detector including a plurality of detector cells extending in a z-axis, said method comprising:

performing a scan;

obtaining data from the detector cells;

performing a trending analysis of the data obtained from the detector cells to predict when a detector will fail the specification.

21. A method in accordance with claim 20 further wherein the data is obtained and analyzed by an automated support center remote from the computed tomography system.

22. A method in accordance with claim 21 wherein performing a trending analysis comprises performing a least squares fit to a linear model of each element of a gain matrix as a function of time.

23. A method in accordance with claim 22 and further comprising utilizing results of the trending analysis to replace the detector prior to its failure.

24. An imaging system comprising an x-ray source and at least one multislice detector module, each detector module including a plurality of detector cells extending in a z-axis, said system configured to:

perform a scan;

obtain data from the detector cells; and to perform a trending analysis to predict when a detector will fail the specification.

25. An imaging system in accordance with claim 24 wherein to perform said trending analysis, said imaging system is configured to perform a least squares fit to a linear model of each element of a gain matrix as a function of time.

26. A multislice computed tomography system comprising an x-ray source for producing an x-ray beam along an imaging plane and a detector comprising a plurality of detector cells extending in a z-axis, said system configured to monitor cell to cell gain variations by:

performing a scan;

obtaining data from the detector cells; and perform a trending analysis to predict when a detector will fail the specification.

27. A system in accordance with claim 26 wherein to perform said trending analysis, said system is configured to perform a least squares fit to a linear model of each element of a gain matrix as a function of time.

* * * * *

UNITED STATES PATENT AND TRADEMARK OFFICE
CERTIFICATE OF CORRECTION

PATENT NO. : 6,327,329 B1  
DATED : December 4, 2001  
INVENTOR(S) : Bromberg et al.

It is certified that error appears in the above-identified patent and that said Letters Patent is hereby corrected as shown below:

Column 6,
Lines 20, 22 and 28, delete "1" and insert therefor -- 6 --.
Lines 57, 59 and 64, delete "7" and insert therefor -- 12 --.

Column 7,
Lines 30 and 32, delete "14" and insert therefor -- 18 --.

Signed and Sealed this

Twenty-third Day of December, 2003

JAMES E. ROGAN
*Director of the United States Patent and Trademark Office*